(12) United States Patent
Bertagnon

(10) Patent No.: US 10,285,787 B2
(45) Date of Patent: May 14, 2019

(54) DENTAL IMPLANT DEVICE

(71) Applicant: DENTAL KNOWLEDGE S.r.l., Milan (IT)

(72) Inventor: Valter Bertagnon, Milan (IT)

(73) Assignee: Dental Knowledge S.R.L. (IT)

(*) Notice: Subject to any disclaimer, the term of this patent is extended or adjusted under 35 U.S.C. 154(b) by 0 days.

(21) Appl. No.: 14/903,493

(22) PCT Filed: Jul. 9, 2014

(86) PCT No.: PCT/IB2014/062971
§ 371 (c)(1),
(2) Date: Jan. 7, 2016

(87) PCT Pub. No.: WO2015/004614
PCT Pub. Date: Jan. 15, 2015

(65) Prior Publication Data
US 2016/0151130 A1  Jun. 2, 2016

(30) Foreign Application Priority Data

Jul. 10, 2013  (IT) .............................. MI2013A1162

(51) Int. Cl.
*A61C 8/00* (2006.01)
*A61C 9/00* (2006.01)
*A61C 13/00* (2006.01)

(52) U.S. Cl.
CPC .......... *A61C 8/0095* (2013.01); *A61C 8/0001* (2013.01); *A61C 8/005* (2013.01);
(Continued)

(58) Field of Classification Search
CPC ..... A61C 8/0095; A61C 8/0001; A61C 8/005; A61C 8/0068; A61C 9/004; A61C 13/004
(Continued)

(56) References Cited

U.S. PATENT DOCUMENTS 5,030,095 A * 7/1991 Niznick ................. A61C 8/005
433/173
5,069,622 A * 12/1991 Rangert ................. A61C 8/005
433/173

(Continued)

FOREIGN PATENT DOCUMENTS

EP  0823243 A2  2/1998
WO  9701306 A1  1/1997
(Continued)

OTHER PUBLICATIONS

International Search Report dated Nov. 3, 2015 in corresponding PCT Patent Application No. PCT/IB2014/062971 filed Jul. 9, 2014.
(Continued)

*Primary Examiner* — Wade Miles
*Assistant Examiner* — Shannel N Wright
(74) *Attorney, Agent, or Firm* — Waller Lansden Dortch & Davis, LLP; Matthew C. Cox

(57) ABSTRACT

This invention refers to a device exploitable within the scope of dental implantology, with specific reference to the set up and to the installation of a multi-teeth fixed prosthesis, either partial or total. The said invention specifically concerns a connection device (1) between a dental implant and the prosthesis. In particular, this invention concerns a connection device (1) including a bearing element (2) and a prosthesis connecting element (3, 3'), with the said connecting element (3, 3') being matchable with the aforementioned bearing element (2), wherein the bearing element (2) includes a base portion (7) on which a conical portion (8) is further positioned and is characterized by the fact that between the base portion (7) and the conical portion (8) a shoulder (12) with a stop portion (13) is formed to prevent relative rotation of the connecting element (3, 3') with respect to the bearing element (2).

4 Claims, 6 Drawing Sheets

(52) U.S. Cl.
CPC ............ *A61C 8/0068* (2013.01); *A61C 9/004* (2013.01); *A61C 13/0019* (2013.01)

(58) Field of Classification Search
USPC ...................................................... 433/201.1
See application file for complete search history.

(56) References Cited

U.S. PATENT DOCUMENTS

| | | | | |
|---|---|---|---|---|
| 5,087,200 A * | 2/1992 | Brajnovic | ............ | A61C 8/0068 433/173 |
| 5,116,225 A * | 5/1992 | Riera | ................... | A61C 8/005 433/173 |
| 5,135,395 A * | 8/1992 | Marlin | ................. | A61C 8/0048 433/173 |
| 5,362,235 A * | 11/1994 | Daftary | ................ | A61C 8/0048 433/172 |
| 5,427,906 A * | 6/1995 | Hansen | ................ | A61C 8/0048 433/173 |
| 5,575,651 A * | 11/1996 | Weissman | ............ | A61C 8/0048 433/173 |
| 5,593,444 A * | 1/1997 | Svensson | ............ | A61C 8/0054 623/17.17 |
| 5,662,474 A * | 9/1997 | Jorneus | ................. | A61C 8/005 433/172 |
| 5,779,480 A * | 7/1998 | Groll | ...................... | A61C 8/005 433/172 |
| 5,810,592 A * | 9/1998 | Daftary | ................. | A61C 8/005 433/172 |
| 5,863,200 A * | 1/1999 | Hamada | ................ | A61C 8/0048 433/173 |
| 5,885,078 A * | 3/1999 | Cagna | ................ | A61C 13/0003 433/172 |
| 6,227,856 B1 * | 5/2001 | Beaty | ................... | A61C 8/0001 433/172 |
| 6,250,924 B1 * | 6/2001 | Luotio | ................. | A61C 8/0048 433/173 |
| 6,343,930 B1 * | 2/2002 | Beaty | ..................... | A61C 8/005 433/173 |
| 6,692,254 B1 * | 2/2004 | Kligerman | ........... | A61C 8/0048 433/173 |
| 6,848,908 B2 * | 2/2005 | Bjorn | ..................... | A61C 8/005 433/172 |
| 7,491,058 B2 * | 2/2009 | Jorneus | ................. | A61C 8/005 433/172 |
| 7,905,727 B2 * | 3/2011 | Kikuchi | ............... | A61C 8/0081 433/172 |
| 8,142,193 B2 * | 3/2012 | Bar Shalom | ........... | A61C 8/005 433/173 |
| 2003/0162149 A1 * | 8/2003 | Bjorn | ..................... | A61C 8/005 433/173 |
| 2005/0266381 A1 * | 12/2005 | Abarno | ................. | A61C 1/084 433/173 |
| 2006/0110706 A1 * | 5/2006 | Jorneus | ................. | A61C 8/005 433/173 |
| 2008/0008981 A1 | 1/2008 | Groll et al. | | |
| 2009/0117520 A1 * | 5/2009 | Kikuchi | ................. | A61C 8/005 433/174 |
| 2009/0298013 A1 * | 12/2009 | Baruc | ..................... | A61C 8/005 433/174 |
| 2010/0330529 A1 * | 12/2010 | Shalom | .................. | A61C 8/005 433/173 |
| 2011/0097687 A1 * | 4/2011 | Engman | ................. | A61C 8/005 433/174 |
| 2013/0084541 A1 * | 4/2013 | von Malottki | ....... | A61C 8/0025 433/174 |
| 2014/0106303 A1 * | 4/2014 | Giasson | ............... | A61C 8/0048 433/173 |
| 2014/0147812 A1 * | 5/2014 | Ilter | ..................... | A61C 8/0001 433/174 |
| 2014/0205969 A1 * | 7/2014 | Marlin | ................. | A61C 8/0001 433/173 |
| 2014/0272797 A1 * | 9/2014 | Prestipino | .............. | A61C 13/34 433/199.1 |
| 2016/0206408 A1 * | 7/2016 | Spindler | .............. | A61C 8/0048 |

FOREIGN PATENT DOCUMENTS

| | | | | |
|---|---|---|---|---|
| WO | | 2010088754 A1 | 8/2010 | |
| WO | WO 2010088754 A1 * | | 8/2010 | ............. A61C 8/005 |

OTHER PUBLICATIONS

Invitation to Pay Additional Fees And, Where Applicable, Protest Fee dated Dec. 9, 2014 in corresponding PCT Patent Application No. PCT/IB2014/062971 filed Jul. 9, 2014.

* cited by examiner

DENTAL IMPLANT DEVICE

FIELD OF THE INVENTION

This invention refers to a device exploitable within the scope of dental implantology, with specific reference to the set up and to the installation of a multi-teeth fixed prosthesis, either partial or total. The said invention specifically concerns a connection device between a dental implant and the prosthesis.

BACKGROUND ART

The techniques normally employed for the construction and the installation of a dental prosthesis, both partial and total, are complex and generally require very long spans of time. After the implant has been positioned in the gingival arch, the procedure is based on several steps including getting the dental impression, installing a temporary prosthesis and substituting the latter with a permanent one. In addition to the fact that the patient is thus obliged to undergo several dental sessions, the procedure requires great skill on the side of the operator as well as of the dental technician, in charge of the material realization of the prosthesis.

Recently, more sophisticated techniques have been gradually gaining ground, which are based on a digital imprint, that is to say on a digital image obtained directly from the patient's mouth. This technique obviously requires very high precision levels.

For a fixed total prosthesis, it is not necessary to proceed with the implant of every single tooth. Indeed, only three or four implants—on whom the complete dental arch prosthesis will be then fixed—can be positioned in the patient's jaw and mandible.

A dental implant consists of a bio-compatible screw, typically in titanium, covered if need be with substances enhancing cohesion, osteointegration and resistance to microbial attack. The implant includes a base section intended to emerge out of the gingival and including an internal thread to fix a connection device the dental bridge will be put on. It is quite rare that the various dental implants necessary for prosthesis reconstruction are positioned in parallel. Typically, the longitudinal axes of dental implants, and, consequently, those of the corresponding connection devices, will be divergent, thus making even more difficult prosthesis design and installation. In particular, after the dental impression has been obtained and the prosthetic bridge has been realized, the correct repositioning of the connection devices functional to the subsequent bridge fixing is practically rather complex.

SUMMARY OF THE INVENTION

This invention aims at realizing a device exploitable all through the various steps of multi-teeth fixed partial or total prosthesis implantology as well as making available a new prosthetic technique able to overcome, at least in part, the difficulties of the prior art.

The said problem is overcome thanks to a connection device for dental implants, as discussed in the attached claims, whose definitions form an integral part of this description.

An object of this invention is thus a connection device for dental implants allowing for an easy assembling on the implant as well as for an equally easy removal and making the subsequent repositioning precise and reproducible.

A further object of the invention is a kit exploitable for multi-teeth fixed prosthesis repositioning and fixing to dental implants.

An additional realization configuration is a method for the design and the production of a multi-teeth fixed prosthesis that relies on the invention's connection device.

Further features and advantages of this invention will result from the description of some embodiments—deemed to be illustrative, but not exhaustive—here below, with specific reference to the following figures.

DETAILED DESCRIPTION OF THE INVENTION

Figure 1:
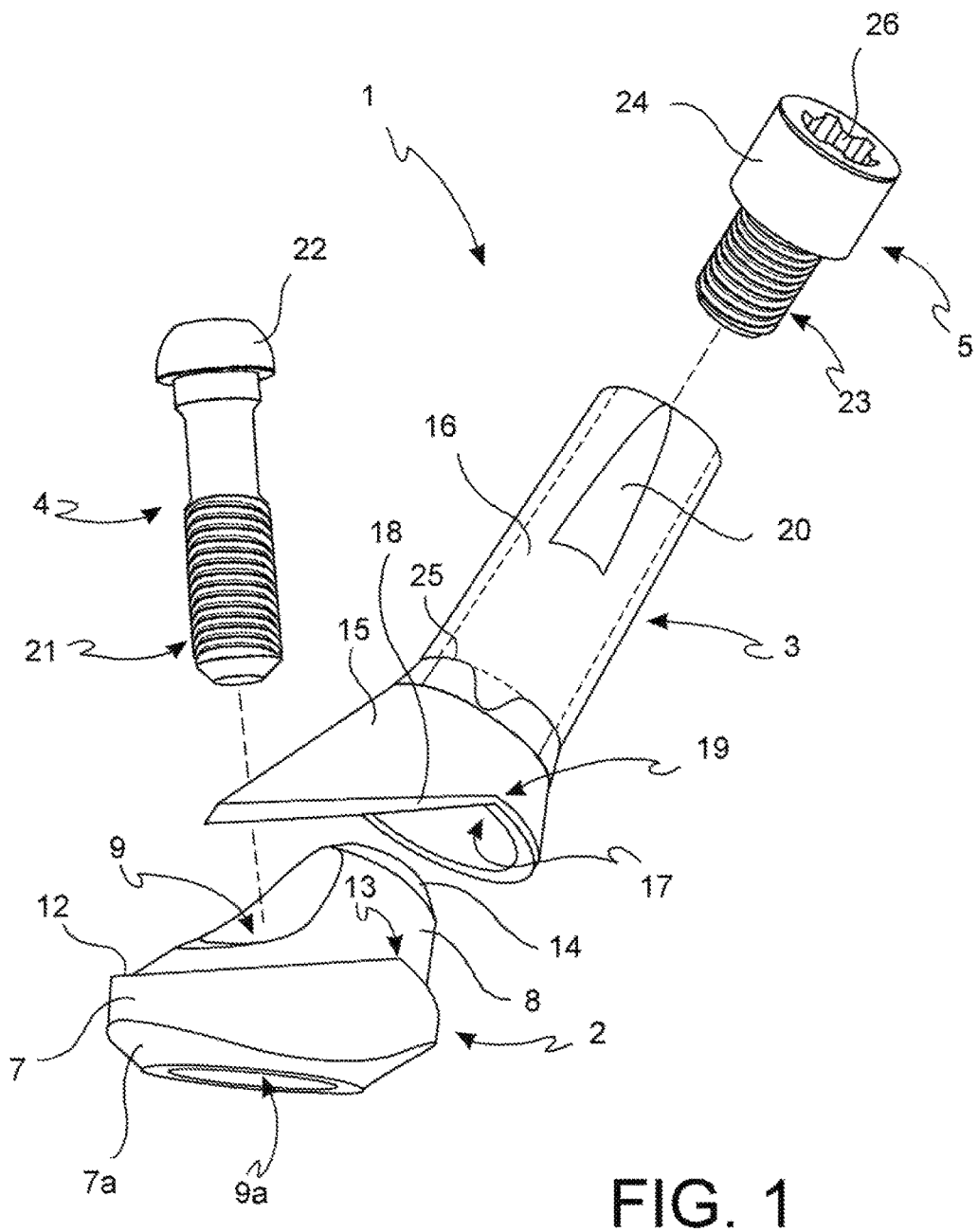
FIG. 1 represents an exploded perspective view of the invention connection device.
Figure 2:
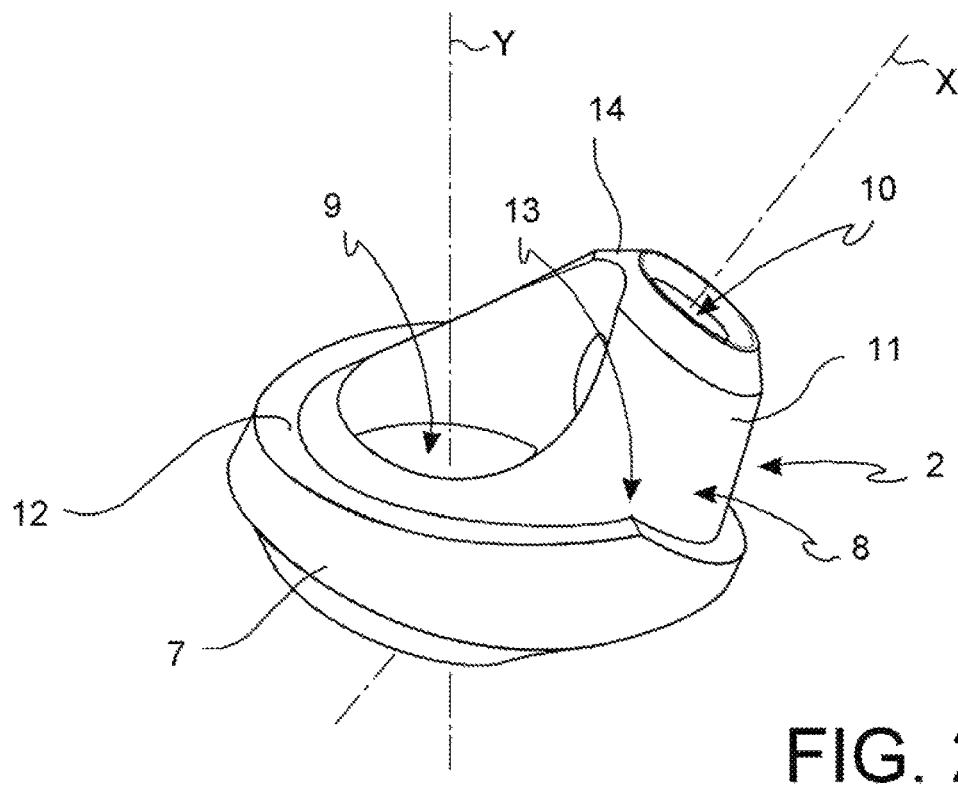
FIG. 2 represents a perspective view of a detail of the connection device displayed in FIG. 1.

With specific reference to FIGS. 1-4, the invention connection device, denoted in its entirety by number 1, includes a bearing device 2, a connection device 3 with a prosthesis, a first fixing screw 4 to anchor the bearing device 2 to a dental implant 6 and a second fixing screw 5 of the connection device 3 to the bearing device 2.

The bearing device 2 includes a base section 7, on which a conic section 8 is located.

The base section 7 includes a lower surface 7a, whose structure and dimensions are adaptable to the most widespread implant screw types available for sale and further has a hole 9a.

The conic section 8 has a first hole 9 aligned with hole 9a belonging to the base section 7 and forming a channel with the latter. Furthermore, the conic section 8 also includes a second hole 10 whose X axis is inclined relative to the Y axis of the first hole 9. The conic section 8 includes a conic surface 11, whose generatrixes go through a generic point of the X axis.

The second hole 10 is threaded internally.

Between the base section 7 and the conic section 8 a shoulder 12 with a block portion 13 is formed, whose major aim will be clarified further ahead in this description.

The block section 13 can be practically realized by changing the slope of the shoulder surface 12 to form a convex profile or a wedge (as shown in the pictures), or a concave or "V" profile. Alternatively, a tooth, a notch or any other blocking element could also be used for that purpose.

The threaded hole 10 has an external edge 14 whose conicity is relatively more marked compared to that of the conic surface 11.

The connection device 3 includes a coupling portion 15 with the bearing device 2, from which an anchor portion 16 for a prosthesis reaches out.

The connection device 3 includes a longitudinal through hole 17 allowing for the introduction of the corresponding fixing screw 5 to the bearing device 2.

The coupling portion 15 has a shape that is complementary to conic portion 8 of the bearing device 2 and further has an edge 18 whose profile shape perfectly matches the shoulder 12.

Based on the embodiment shown in the figures, the edge profile 18 has a V-shaped portion 19 complementary to the wedge profile of the shoulder's 12 block portion 13.

The anchor section 16 has a substantially cylindrical or slightly frusto-conical shape and has a reference mark 20 on the external surface.

The fixing screw 4 connecting the bearing device 2 to the implant is a screw like those commonly used for this type of implementation and has a thread 21 matchable with the internal thread of the implant screw head and a head 22 with a notch suited to a Phillips screwdriver C1 or of any other conventional type.

The fixing screw 5 of the connection device 3 to the bearing device 2 is a screw like those commonly used for these types of implementations and has a thread 23 matchable with the threaded hole 10 of the bearing device 2 and a head 24 which is substantially cylindrical and jutting out relative to the thread 23, so as to function as a block device against a shoulder 25 within the connection device 3 hole 17. The head 24 of the fixing screw 5 further includes a notch 26 suited to a Phillips screwdriver C2 or, in other embodiments, to any other type of screwdriver.

Figure 3:
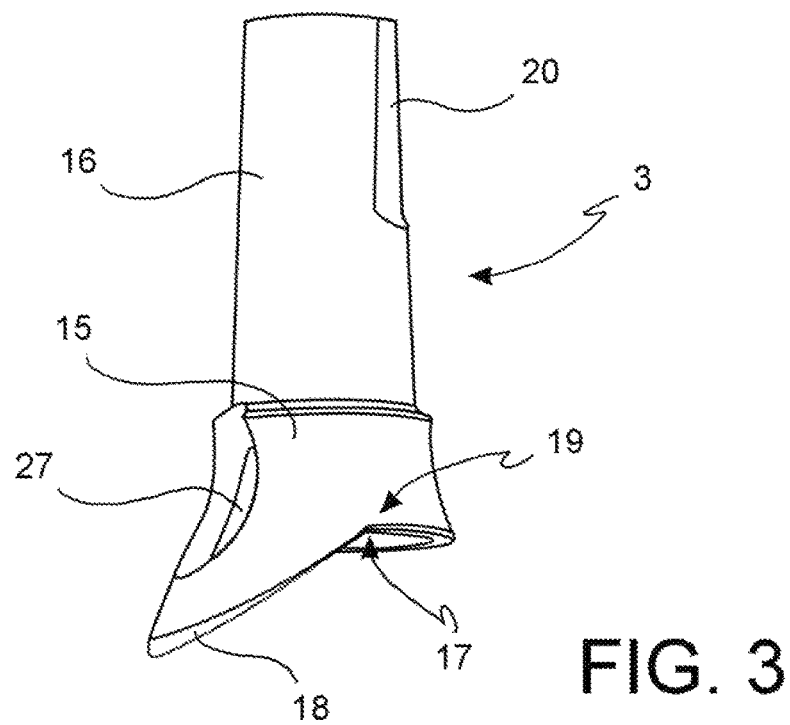
FIG. 3 represents a perspective view of a second detail of the connection device displayed in FIG. 1, according to a different embodiment.

In a different embodiment, shown in FIG. 3, the connection device 3' is identical in all respects to the one shown in FIG. 1, apart from the fact of including a through hole 27 on the coupling portion 15, perfectly aligned with the hole 9 of the conic portion 8 of the bearing device 2, whenever the latter and the connection device 3' are assembled together.

Figure 4:
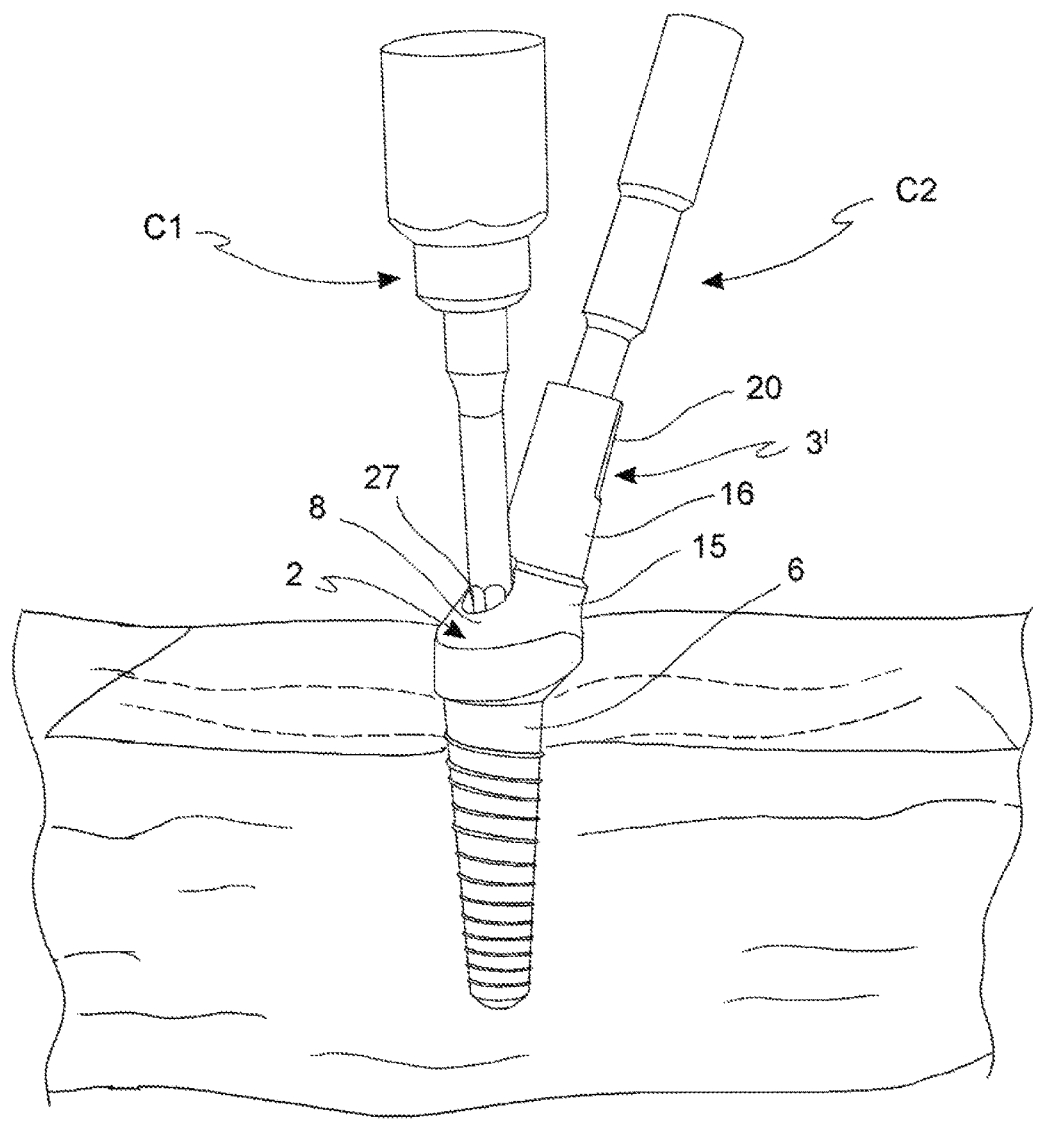
FIG. 4 represents a perspective view of the connection device during the assembling step on a dental implant.

As displayed in FIG. 4, the through hole 27 of the connection device 3' allows for the screwing or the unscrewing of the bearing device 2 of the implant I, with no need to remove the connection device 3' preliminarily. The advantage of this solution will be clarified further ahead in this description.

The bearing device 2, the connection device 3, 3' and the corresponding fixing screws 4, 5 are typically realized in titanium or titanium alloys (e.g. grade 5 titanium), medical chromium, or any other bio-compatible material suited to these implementations.

We will now describe the design and realization method of a multi-teeth fixed prosthesis in line with this invention, for instance, to replace a mobile prosthesis (bridge or total), once the dentist has provided for the installation of the necessary implant screws 6 within a patient's oral cavity.

Figure 5:
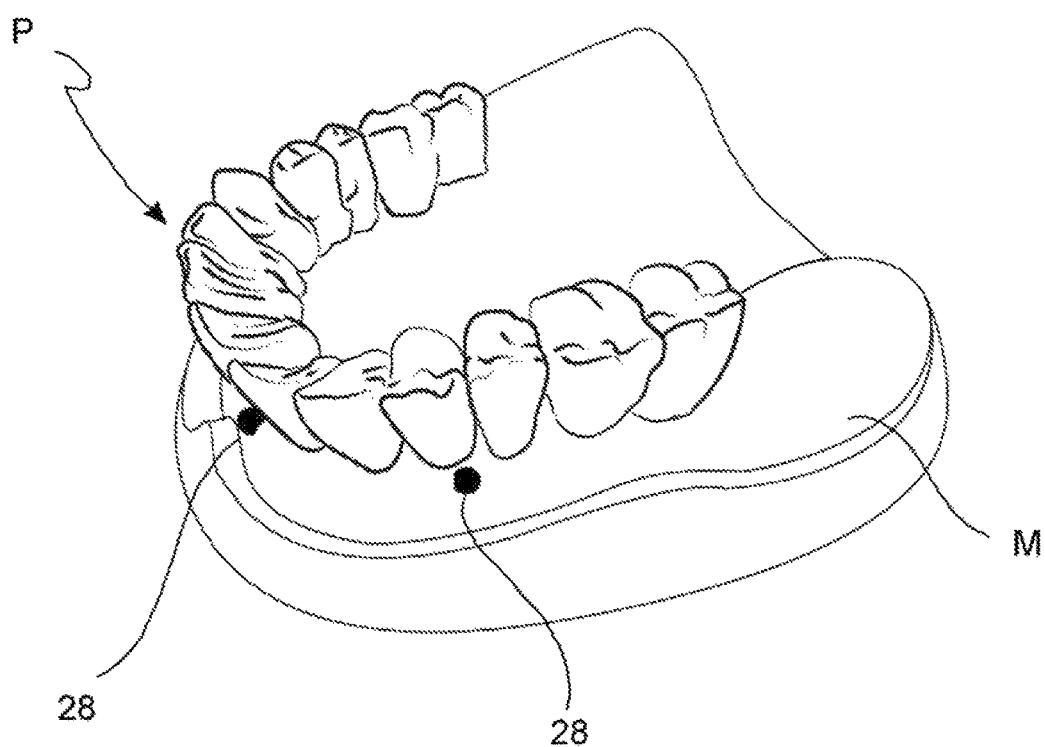
FIG. 5 represents a perspective view of a patient's jaw.

FIG. 5 displays as an example a patients' jaw M, on which a temporary prosthesis or an old bridge P are present. Three reference points 28 are attached on the gum (only two reference points 28 are visible, the third being approximately located in a symmetrical position with respect to the first point on the right).

In certain embodiments, the reference points 28 are made up of small semi-spheres, for instance in some plastic material, stuck on the mucosa through stick adhesives, like for instance medical grade cyanoacrylate or polymethacrylate.

At this point, you perform a first digital vestibular scan of both jaw M with three reference points 28, and of the mandible (not drawn), so as to obtain a digital image of the vestibular oral cavity of the patient.

In some realization configurations the three reference points 28 can be placed also or only on the mandible.

The digital scan can be performed by means of a scanner or a camera of the type used in dental applications.

After the implant screws 6 (usually four in the case of a fixed total prosthesis) were fixed on the gingival arch of a patient, if not already present, on each of them is screwed the bearing element 2. Onto the support element 2 can be screwed in advance the drilled connection element 3' Indeed, thanks to the hole 27 it is possible to insert the fixing screw 4 into the hole 9-9a of the bearing element 2 (FIG. 4), possibly using the anchoring portion 16 of the connection element 3' as a handle of the device. In fact, being the bearing element 2 small and therefore difficult to handle, its mounting on the screw implant 6 may present difficulties.

Figure 6:
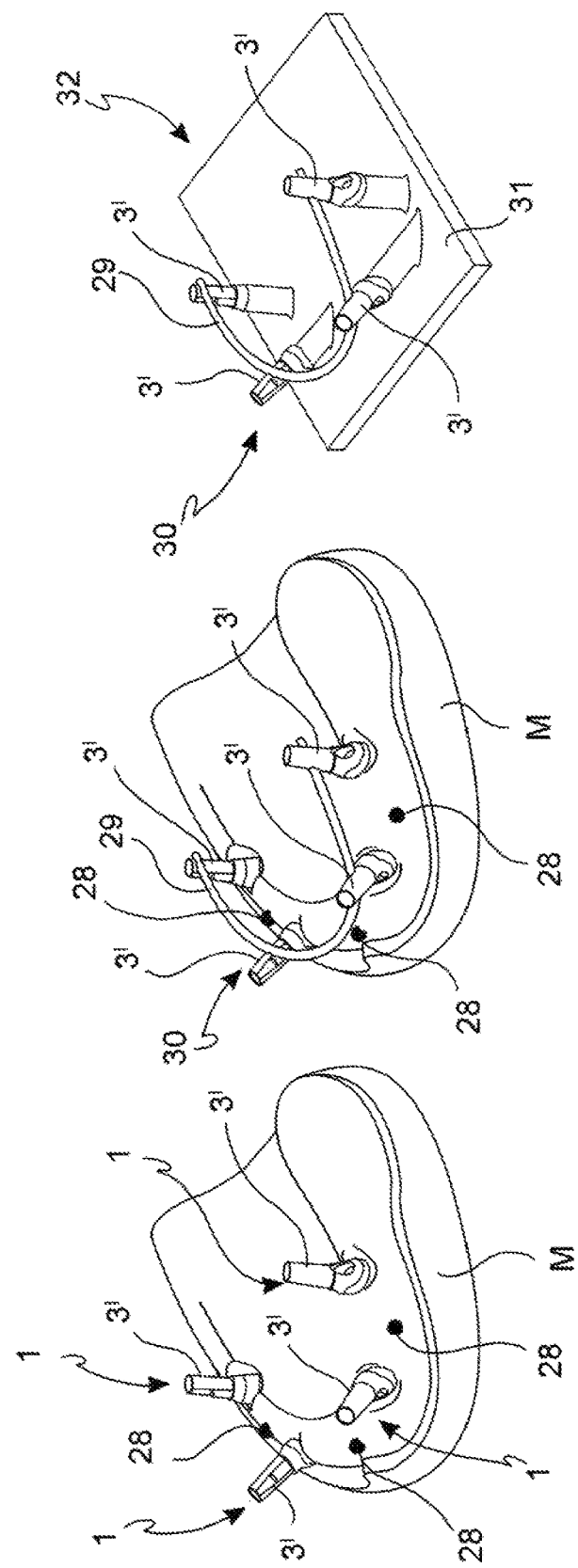
FIGS. 6A, 6B and 6C represent perspective views of a sequence of steps aimed at the realization of a fixed total prosthesis.

The jaw of the patient M on which were mounted the bearing elements 2 associated with the drilled connection elements 3' which is shown in FIG. 6A. Also visible are the three points of reference 28 still positioned on the gingival mucosa. As can be seen, the axes of the connecting elements 3' are not parallel.

The presence on the bearing elements 2 of the stopping portion 13, which interacts with the edge 18 of the connection element 3', allows to avoid the rotation of the latter about the axis X, thus making reproducible and uniquely determined its position relative to the support element 2. The reference notch 20 present on the surface of the anchoring portion 16 allows the identification of the correct position of the connection devices 1 in the oral cavity.

At this point, you perform a second digital scanning of the whole mouth, so as to obtain a digital image of the total of the oral cavity with the connection devices 1 mounted. The three reference points 28 allow the comparison of this digital image with that taken earlier.

A bar 29 of a ductile material (resin or metal, preferably with a non-circular section) is shaped so as to connect the various connection devices 1 mounted on the jaw M, then the shaped bar 29 is affixed thereto, for example by means of a self-curing resin, so as to obtain a jig 30 (FIG. 6B).

We proceed to the removal of the jig 30 from the oral cavity of the patient. This operation involves first the unscrewing of the various connecting elements 3' by the respective bearing elements 2, so as to remove the jig 30. Such removal, as well as the subsequent repositioning, is permitted by the coupling between the conical connection elements 3' and bearing elements 2, despite the fact that the various connecting elements 3' are offset with respect to one another. Subsequently, the individual bearing elements 2 are in turn unscrewed from relative implants 6 and removed from the oral cavity.

The bearing elements 2 are then mounted on analogues of the implant screws 6 present in the patient's mouth and then the jig 30 is repositioned on them. The jig 30 with the bearing elements 2 is then placed on a base 31, on which the analogs of the implant screws 6 are fixed for example by means of a self-curing resin, obtaining the exact repetition of the implant positions (between them) inserted in the oral cavity a model 32 (FIG. 6C) M of the jaw of the patient.

Using an appropriate CAD/CAM software, of the type used in dental applications, we will proceed with the following steps:

i) comparison of the digital vestibular images of the patient's oral cavity arising from the first and second scan;

ii) design of multiple fixed prosthesis 34 through CAD/CAM systems on the basis of the comparison of step i) in order to create a project file;

iii) execution of multiple fixed prosthesis on the basis of the design at point ii).

In step ii), the comparison between the images of the first and second scan allows to design the prosthesis together with the holes 33 adapted to mate with the connection devices 1 of the invention, in particular with the respective connection elements 3.

The realization of the prosthesis according to step iii) can be made according to conventional methods known to skilled dental technician or by automated methods of milling (removal of material) or 3D printing (adding material) from the project file prepared in step ii).

Figure 7:
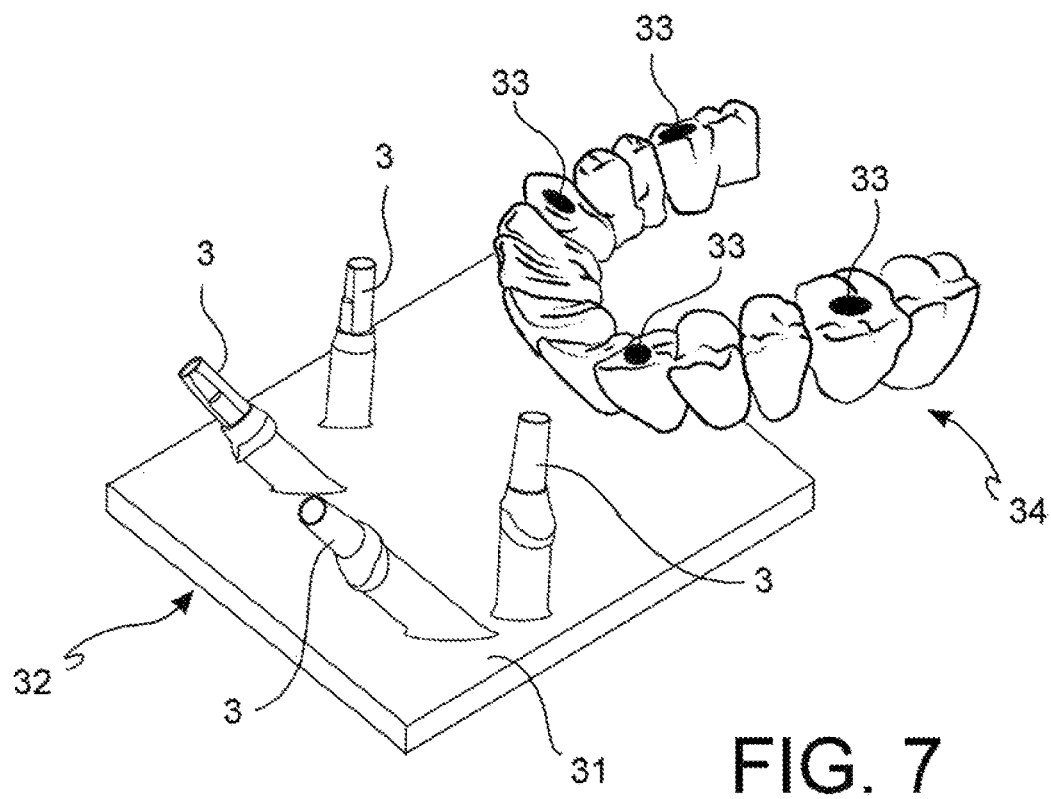
FIG. 7 represents a perspective view of the assembling step of a fixed total prosthesis with the invention connection devices.
Figure 8:
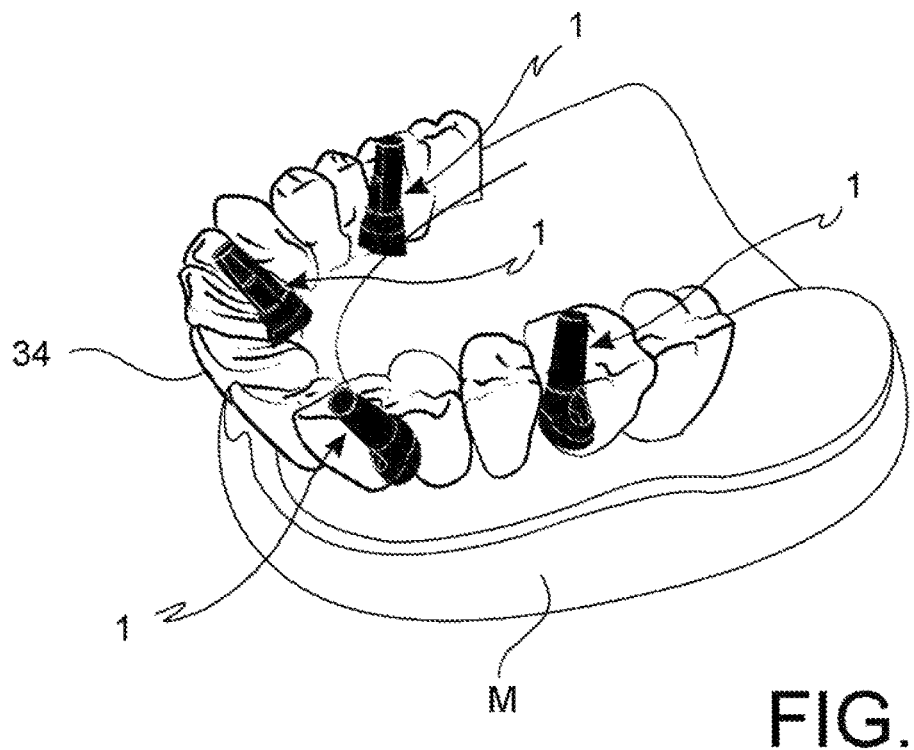
FIG. 8 represents a perspective view in transparency of a fixed total prosthesis assembled on a patient's jaw.

The method then provides for the following steps:
removing from the template model 32 the jig 30 with the drilled connecting elements 3' and mounting on its bearing elements 2 of the model 32 the non-drilled connecting elements 3;
mounting the prosthesis 34 on the connecting elements 3 of the model 32 by inserting the connecting elements 3 into the respective holes 33 (FIG. 7) and securing it for example by gluing with dental sealants;
unscrewing the elements of connections 3, and then the prosthesis 34 rigidly coupled thereto, from the model 32;
reassembling the jig 30 with the drilled connecting elements 3' on the model 32;
Removing from the model 32 the jig 30 together with the bearing elements 2, using the hole 27 of the connecting elements 3' to unscrew them from the analogues of implant screws 6;
repositioning in the patient's mouth the jig 30, fixing the bearing elements 2 to the implant screws 6;
Removing the jig 30 by unscrewing the connection elements 3' from the bearing elements 2;
Mounting on the bearing elements 2 in the oral cavity of the patient the prosthesis 34.

The same process will be repeated on the mandible.

The process described above provides a digital imprint made by the digital scanning of the patient's oral cavity and the related acquisition of digital images. The process of the invention that uses the connection devices 1 described above can however also be adapted in case you want to follow a traditional method for the replacement of a fixed prosthesis with a mobile prosthesis, once the clinician has put in the patient's mouth the implants 6. In this case it will be possible to go through the following operational steps:

A) mounting on the implant screws 6 positioned on a gingival arch of the oral cavity of the patient the bearing elements 2 together with the drilled connection elements 3' as shown in FIG. 4 and as previously described. Before tightening, the bearing elements 2 must be turned on implants 6 so as to make the relative connection element 3' assume the more palatal position as possible;

B) adapting the old denture or a copy thereof to the drilled connecting elements 3' mounted, making on it special holes 33;

C) performing additional holes in the old prosthesis or its copy in cestibular and palatal positions;

D) replacing in the patient's mouth the drilled connecting elements 3' with not-drilled connecting elements 3;

E) mounting the old denture drilled according to B) and C) on the non-drilled connecting elements 3 and fixing it to them, for example through self-curing resin;

F) taking the impression of gingival mucosa by inserting into the vestibular and palatal holes according to phase C) some prosthetic silicone;

G) removing the old mobile denture with the footprint of the gingival mucosa by unscrewing the connecting elements 3 by the respective bearing elements 2, thus realizing a jig with the mucous imprint and the bite registration between the maxillary and mandible using the occlusal surface of the old prosthesis;

H) mounting on the jig created in step G) analogues of implant screws 6 fixed to the bearing members 2;

I) realizing the plaster model of the dental arch of the patient and his antagonist.

Obviously the same process can be performed both starting from the jaw or from the mandible and thereby realizing the plaster model also of the antagonist, according to conventional techniques well known to the expert dental technician.

The process described above allows the use of the old prosthesis as a template for repositioning and as individual print-holder for the construction of the plaster model.

A further object of the invention is a kit for the design and the realization of a multiple fixed prosthesis comprising:
One or more bearing elements 2;
One or more non-drilled connecting elements 3;
One or more drilled connecting elements 3';
Optionally, one or more bars 29 of a ductile material, such as a resin or a metal;
Optionally, one or more base tablets 31;
Optionally, one or more fixing screws 4, 5 for the bearing elements 2 to an implant 6 and for the connection elements 3, 3' to the bearing elements 2;
Optionally, an amount of auto-locking resin.

The connection device 1 according to the invention simplifies the assembly and design/construction of a fixed prosthesis, allowing a precise repositioning without errors of the connecting elements 3, 3' on the bearing elements 2 and of the latter on the implant screws.

It's obvious that have been described only some particular forms of embodiment of the present invention, where the expert of the art will be able to make all those modifications necessary for its adaptation to particular applications, without thereby departing from the scope of protection of the present invention.

The invention claimed is:

1. Connection device (1) comprising:
a bearing element and a connecting element for a prosthesis, said connecting element being apt to be coupled to said bearing element and the connecting element having a first edge with a first profile facing the bearing element, in which the bearing element comprises a base portion on which is disposed a conical portion, including between the base portion and the conical portion a shoulder which has a stop portion including a change of inclination of the shoulder, wherein the shoulder and the stop portion of the bearing element match the edge profile of the connecting element to prevent relative rotation of the connecting element with respect to the bearing element;
wherein the conical portion comprises a first hole having an axis (Y) and a second hole, internally threaded, having an axis (X) inclined with respect to the axis (Y) of the first hole,
wherein the connecting element comprises a coupling portion with the bearing element, by which extends an anchoring portion for a prosthesis, wherein said coupling portion has a shape complementary to the conical portion of the bearing element and has a second edge having a second profile shaped to couple with the shoulder, wherein the connecting element comprises a longitudinal through hole which allows the introduction of a fastening screw for the bearing element, and wherein the connecting element comprises on the coupling portion a through hole such as to be in alignment with the first hole of the conical portion of the bearing element when the bearing element and the connecting element are mounted together, and such as to allow for the screwing or the unscrewing of the bearing element with no need to remove the connection element preliminarily.

2. Connection device according to claim 1, wherein the change of inclination of the shoulder forms a convex or a concave profile or wedge-shaped or V-shaped profile.

3. Connection device according to claim 1, wherein the conical portion comprises a conical surface oriented co-axially with the axis (X).

4. Connection device according to claim 1, wherein the anchoring portion comprises on an outer surface a reference mark.

\* \* \* \* \*